United States Patent [19]

Akhavi

[11] 4,266,751
[45] May 12, 1981

[54] STRIPPER CLAMP

[75] Inventor: David S. Akhavi, Los Angeles, Calif.

[73] Assignee: American Hospital Supply Corporation, Evanston, Ill.

[21] Appl. No.: 26,117

[22] Filed: Apr. 2, 1979

[51] Int. Cl.³ .............................................. F16L 55/14
[52] U.S. Cl. .......................................... 251/6; 251/10; 222/102
[58] Field of Search ........................... 251/4, 6, 9, 10; 222/102

[56] References Cited

U.S. PATENT DOCUMENTS

| 1,983,462 | 12/1934 | Johnson | 222/102 |
| 3,099,429 | 7/1963 | Broman | 251/6 |
| 3,194,452 | 7/1965 | Sanderford | 251/9 X |
| 3,847,370 | 11/1974 | Engelsher | 251/6 |

Primary Examiner—William R. Cline
Assistant Examiner—H. Jay Spiegel
Attorney, Agent, or Firm—Larry N. Barger

[57] ABSTRACT

A clamp with an exposed roller for manually rolling along a flexible tube to express the tube's contents. The stripper clamp is useful for one-handed movement toward a dispensing end of a flexible tube blood reservoir.

3 Claims, 7 Drawing Figures

U.S. Patent    May 12, 1981    4,266,751
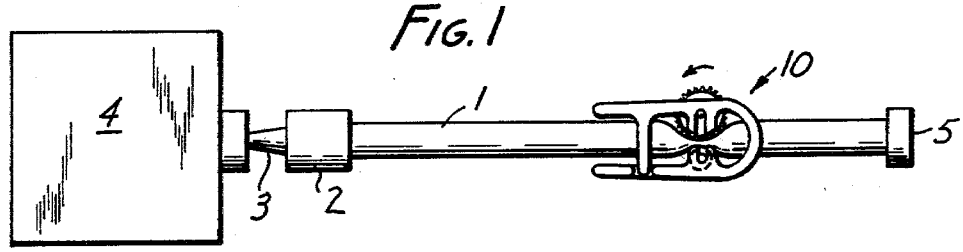
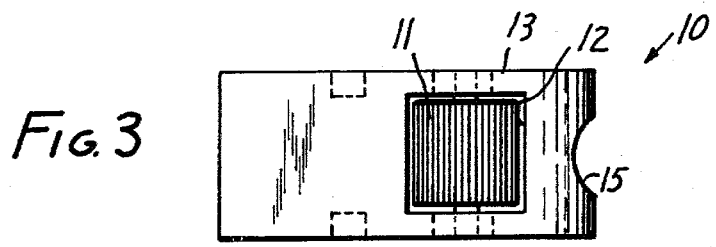
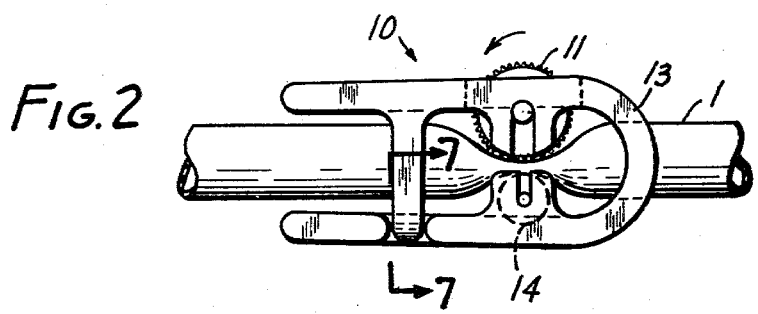
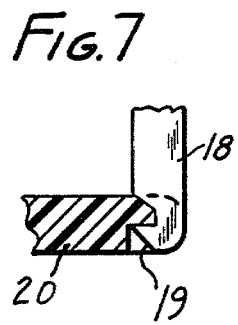
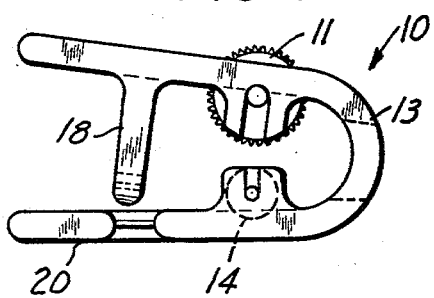
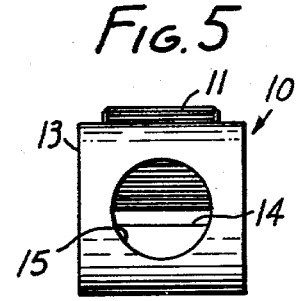
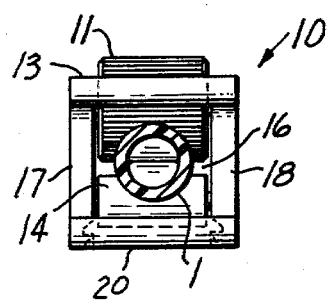

STRIPPER CLAMP

BACKGROUND

U.S. Pat. Nos. 3,194,452 and 3,847,370 describe tube stripping clamps which have internal rollers. These clamps are primarily useful for pulling along a flexible tube to strip out its contents. Such clamps are not useful for one-handed operation for pushing the contents out of such tube. Such pushing action would simply buckle the tube.

U.S. Pat. No. 3,099,429 describes a typical roller clamp in which a firm actuated roller and floor of the clamp are inclined toward each other to vary the flow rate of liquid through such tube. Such roller clamps remain basically stationary on the tube and do not act to strip out the tube's contents by longitudinal rolling action along the tube.

In a co-pending co-owned application entitled "Blood Sampler," Ser. No. 025,980, filed Apr. 2, 1979, a flexible tube blood collector is described which is used to dispense a blood sample into a testing machine. Also in a co-pending, co-owned application entitled "Method of Collecting and Dispensing A Blood Sample," Ser. No. 025,979, filed Apr. 2, 1979, the method is described and claimed. When the machine does not have a vacuum extractor for the blood sample, the blood sample must be stripped from the tube into the machine. Because the stripper clamp is moving with a pushing action, it is important not to buckle the tube as the clamp proceeds toward the machine. Previous stripper clamps required a two-handed stripping; i.e., one to hold the tube taut to prevent buckling and the other to slide the clamp.

SUMMARY OF THE INVENTION

The present invention overcomes the problem with previous stripper clamps and provides a stripper clamp that is operable with one hand by rolling an exposed roller along the clamp. The stripper clamp of this invention also has a body which is openable and closable against a flexible blood sampler tube to segment blood within the tube.

THE DRAWINGS

FIG. 1 is a side elevational view of the stripper clamp mounted on a blood sampling device connected with a blood testing machine;

FIG. 2 is an enlarged side elevational view of the stripper clamp in closed position;

FIG. 3 is a top elevational view of the clamp;

FIG. 4 is a side elevational view of the stripper clamp in open position;

FIG. 5 is a right end view of the stripper clamp in closed position;

FIG. 6 is a left end view of the stripper clamp in closed position; and

FIG. 7 is an enlarged sectional view taken along line 7—7 of FIG. 2.

DETAILED DESCRIPTION

In FIG. 1, a flexible tubular blood reservoir 1 is connected to a needle adapter 2 which has a hollow protrusion 3 that connects to a blood analyzing machine 4. Blood is collected, such as from an artery, through a needle (not shown) on adapter 3. Blood pressure causes the blood sample to fill the flexible tubular reservoir 1 while forcing air in the tube to exit through a filtered vent at a rear portion 5 of the tube. The blood flows through the tube while a clamp, shown generally at 10, is in open position. The clamp is closed to pinch the resilient tube and segment the blood sample. The specific structure of the blood sampler is disclosed in the above identified co-pending application.

In some blood analyzing machines, a vacuum extractor fits inside the adapter 3 and sucks out the measured quantity of blood. In other machines with no vacuum extractor, the flexible tube must be stripped toward the machine to dispense the blood sample. Unlike most stripper clamps which are operated with a pulling motion, this stipper clamp is operated with a pushing motion toward the blood analyzing machine 4. This creates a particular problem because of the flexibility of resilient tube 1 which can buckle with a simple pushing motion on clamp 10. To overcome this, it is necessary to place one hand on a rear portion 5 of the blood collecting tube to hold it in taut position while pushing a clamp toward the machine with the operator's other hand. This is a cumbersome two-handed operation.

The present clamp shown in FIG. 2 has an exposed roller 11 that extends through an opening 12 in a top wall of a U-shaped body member 13. A secondary roller 14 opposite roller 11 can form a pinching action on resilient tubular reservoir 1. As the roller 11 is moved in the direction of the arrow with thumb motion across the roller 10 and the adjacent table surface longitudinally disposed relative to the opening for roller 10 in the top arm, the clamp 10 advances toward the blood analyzing machine without buckling the tubular reservoir 1.

As shown in FIG. 4, the generally U-shaped body of the clamp has a natural open position which provides sufficient passage for a contained tube to prevent liquid to pass the clamp area. Preferably, the clamp has a slight compressive fit on the tube to prevent its unintentional longitudinal sliding along the tube when in its open position. During collection of the blood sample from a patient, the clamp would be in the open position.

An opening 15 in a rear of the clamp and an opening 16 between locking legs 17 and 18 forward of the roller 11 provides an opening through which the tubular reservoir 1 can extend.

Each of locking legs 17 and 18 has a snap lock structure such as shown in FIG. 7 where a tapered lead-in surface 19 causes the leg 18 to flex and snap onto one arm 20 of U-shaped clamp 13.

The stripper clamp body and rollers can be very conveniently molded of a thermoplastic material.

In the foregoing description, a specific example has been used to illustrate the invention. However, it is understood by those skilled in the art that certain modifications can be made to this example without departing from the spirit and scope of the invention.

I claim:

1. A stripper clamp mounted on a blood collection tube, wherein the clamp comprises: a generally U-shaped body having a pair of opposed arms; one arm having a first transverse roller mounted thereon and being confined within the space between the opposed arms; the opposite arm having a second transverse roller which protrudes through an opening in such second arm, and which second roller is adapted to be rolled by an operator's hand to move the clamp along the tube; said U-shaped body having an arm connecting portion located rearwardly of the rollers; locking means for securing the opposed arms together at a location forwardly of the rollers, said locking means including a pair of spring biased legs straddling the blood collection tube; and snap fit retaining means on the body for receiving the straddling spring biased legs and thereby clamping the opposed rollers about the blood collection tube.

2. A stripper clamp and tube combination as set forth in claim 1, wherein the stripper clamp has a normally open position that lightly grips the flexible tube to prevent inadvertent sliding along the tube, but which does not close off a passage through such tube.

3. A stripper clamp and flexible tube combination as set forth in claim 1, wherein the tube is adapted to collect and dispense a blood sample.

* * * * *